(12) United States Patent
Mack et al.

(10) Patent No.: US 6,395,858 B1
(45) Date of Patent: May 28, 2002

(54) AMINOPROPYL-FUNCTIONAL SILOXANE OLIGOMERS

(75) Inventors: Helmut Mack; Dieter Barfurth, both of Rheinfelden; Roland Edelmann, Wehr; Albert-Johannes Frings, Rheinfelden; Michael Horn, Rheinfelden; Peter Jenkner, Rheinfelden; Ralf Laven, Schwoerstadt; Jaroslaw Monkiewicz, Rheinfelden; Burkhard Standke, Loerrach, all of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/427,479

(22) Filed: Oct. 27, 1999

(30) Foreign Application Priority Data

Oct. 27, 1998 (DE) .......................... 198 49 308

(51) Int. Cl.[7] .............................................. C08G 77/26
(52) U.S. Cl. ............................. 528/38; 528/33; 528/37; 556/413; 556/425; 556/450; 556/460; 556/466
(58) Field of Search .............................. 528/33, 37, 38; 556/413, 425, 450, 460, 466

(56) References Cited

U.S. PATENT DOCUMENTS

| 3,045,036 A | * | 7/1962 | Jex et al. |
| 4,892,918 A | * | 1/1990 | Ryang .......................... 528/15 |
| 5,282,998 A | * | 2/1994 | Horn et al. ............. 252/182.14 |
| 5,629,400 A | * | 5/1997 | Standke et al. ................ 528/38 |
| 5,679,147 A | * | 10/1997 | Standke et al. ........ 106/287.11 |
| 5,932,757 A | * | 8/1999 | Standke et al. ............. 556/457 |
| 6,133,466 A | * | 10/2000 | Edelmann et al. ........... 556/440 |

FOREIGN PATENT DOCUMENTS

| DE | 196 24 032 | 12/1997 |
| EP | 0 518 057 | 12/1992 |
| EP | 0 675 128 | 10/1995 |
| EP | 0 716 127 | 6/1996 |
| EP | 0 726 128 | 6/1996 |

* cited by examiner

Primary Examiner—Robert Dawson
Assistant Examiner—Jeffrey B. Robertson
(74) Attorney, Agent, or Firm—Oblon, Spivak, McClelland, Maier & Neustadt, P.C.

(57) ABSTRACT

The present invention relates to mixtures of catenate and cyclic siloxane oligomers of the formulae I and II

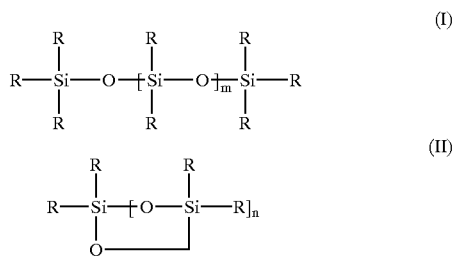

where the substituents R consist of (i) aminopropyl-functional groups of the formula —$(CH_2)_3$—$NH_2$ or —$(CH_2)_3$—$NHR'$ or —$(CH_2)_3$—$NH(CH_2)_2$—$NH_2$ or —$(CH_2)_3$—$NH(CH_2)_2$—$NH(CH_2)_2$—$NH_2$, in which R' is a linear, branched or cyclic alkyl group of 1 to 18 carbon atoms or an aryl group of 6 to 12 carbon atoms, and (ii) methoxy, ethoxy, 2-methoxyethoxy and/or propoxy groups, and (iii) if desired, alkyl, alkenyl, isoalkyl or cycloalkyl groups of 1 to 18 carbon atoms and/or aryl groups of 6 to 12 carbon atoms, and where not more than one aminopropyl-functional group is attached to one silicon atom and the degree of oligomerization of compounds of the formula I is within the range 2<m<30 and that of compounds of the formula II is 3≦n≦30 and the quotient of the molar proportion of Si/alkoxy group is ≧0.5. The present invention also relates to a special process for preparing said mixtures and to their use.

29 Claims, No Drawings

AMINOPROPYL-FUNCTIONAL SILOXANE OLIGOMERS

BACKGROUND OF THE INVENTION

1. Field of the Invention

The present invention relates to compositions containing mixtures of catenate and cyclic siloxane oligomers of the formulae I and II:

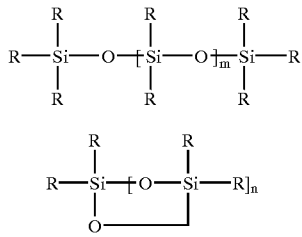

where the R substituents comprise both alkoxy groups and organofunctional groups, and where not more than one organofunctional group is attached to one silicon atom.

The present invention also relates to a process for preparing the mixtures and to their use in a variety of applications.

2. Description of the Background

Mixtures of catenate and cyclic siloxane oligomers are obtained, for example, by controlled hydrolysis or condensation of organofunctional alkoxysilanes. A particular problem when preparing multifunctional siloxane oligomers is the highly differing hydrolysis or condensation behavior of the individual organoalkoxy or organochlorosilanes.

EP 0 716 128 A2, EP 0 716 127 A2 and EP 0 675 128 2 A1 disclose aqueous solutions of amino-functional and CH-containing organosilanes and organosiloxanes. In these organosilane systems, hydrolysis is virtually complete.

EP 0 518 057 A1 and DE 196 24 032 A1 disclose mixtures of catenate and cyclic vinyl- and also alkyl-functional siloxane oligomers which also carry alkoxy groups. Such mixtures are employed, for example, to hydrophobicize mineral surfaces and pulverulent substances, and as crosslinking agents for thermoplastic polyolefins.

German patent application serial number 198 34 990.4 describes mixtures of catenate and cyclic acryloxypropyl- or methacryloxypropyl-functional siloxane oligomers.

Such siloxane oligomer mixtures can be used, for example, for the surface treatment of mineral surfaces or pulverulent substances, such as titanium dioxide, talc, clay, silicas, quartz, kaolin, aluminum hydroxide, magnesium hydroxide, bentonite, montmorillonite, mica (muscovite mica), calcium carbonate (chalk, dolomite), for example. These siloxane oligomer mixtures are also employed as adhesion promoters in, for example, kaolin-filled rubber compounds.

However, there still remains a need for new compositions containing siloxane oligomers.

SUMMARY OF THE INVENTION

It is an object of the present invention to provide novel organofunctional siloxane oligomer mixtures, containing amino-functionalized siloxane compounds.

It is another object of the invention to provide methods of making the mixtures.

It is another object of the invention to provide methods of using the mixtures for a variety of purposes.

The objects of the invention, and others, may be accomplished with a mixture of catenate and cyclic siloxane oligomers of the formulae I and II:

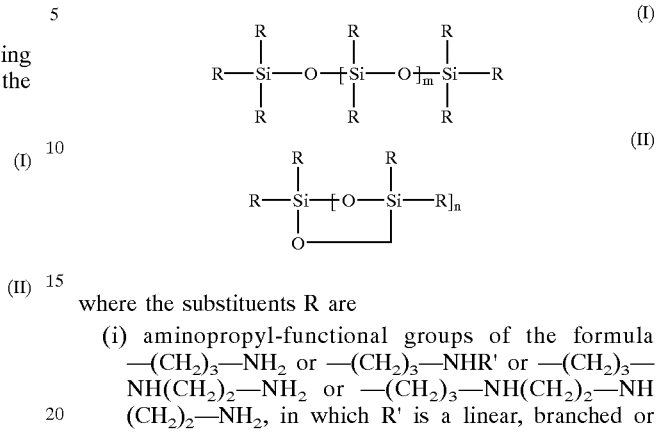

where the substituents R are (i) aminopropyl-functional groups of the formula —(CH$_2$)$_3$—NH$_2$ or —(CH$_2$)$_3$—NHR' or —(CH$_2$)$_3$—NH(CH$_2$)$_2$—NH$_2$ or —(CH$_2$)$_3$—NH(CH$_2$)$_2$—NH(CH$_2$)$_2$—NH$_2$, in which R' is a linear, branched or cyclic alkyl group of 1 to 18 carbon atoms or an aryl group of 6 to 12 carbon atoms, and (ii) methoxy, ethoxy, 2-methoxyethoxy and/or propoxy groups, and (iii) if desired, alkyl, alkenyl, isoalkyl or cycloalkyl groups of 1 to 18 carbon atoms and/or aryl groups of 6 to 12 carbon atoms, where not more than one aminopropyl-functional group is attached to one silicon atom, the degree of oligomerization of compounds of the formula I is within the range $2<m<30$ and that of compounds of the formula II is $3 \leq n \leq 30$, and the quotient of the molar proportion of Si/alkoxy group is $\geq 0.5$.

Such mixtures may be obtained by a controlled reaction using at least one aminopropyl-functional trialkoxysilane or one aminopropyl-functional methyldialkoxysilane as component A and, if desired, at least one alkyl-, alkenyl-, isoalkyl- or cycloalkyl-trialkoxysilane of 1 to 18 carbon atoms and/or phenyltrialkoxysilane and/or alkyl-, alkenyl-, isoalkyl- or cycloalkyl-methyldialkoxysilane of 1 to 18 carbon atoms and/or phenylmethyldialkoxysilane as component B and, if desired, a tetraalkoxysilane as component C, subjecting the components A and—if used—B and C in succession or in a mixture to controlled hydrolysis and condensation using from 0.6 to 1.2 mol. of water per mol. of Si and from 0.1 to 5 times the amount by weight of methanol and/or ethanol, based on the alkoxysilanes employed, at a temperature from 10 to 95° C. and subsequently working up the product mixture by distillation under atmospheric pressure or under reduced pressure and at a liquid-phase temperature of up to 120° C. In the course of this distillation the free alcohol and any residues of the unhydrolyzed monomeric starting materials are suitably removed from the product. It is possible, accordingly, to provide a further amino-functional siloxane oligomer mixture. A particular advantage is that the hydrolysis or condensation can be carried out in a controlled manner without an additive alien to the system, such as a hydrolysis or condensation catalyst.

The objects of the present invention may also be accomplished with methods of using the compositions containing the siloxane mixtures described above. Such methods of use include the following:

(1) a method of improving the adhesion properties of adhesives and sealants, by incorporating the composition into an adhesive or a sealant, (2) a method of modifying organic resins, by contacting an organic resin with the composition, (3) a method of crosslinking organic resins, by contacting the organic resins with the composition, (4) a method of providing binders in inks and coatings, by incorporating the composition into an ink or a coating, (5) a method of coating glass fibers, by applying the composition to glass fibers, (6) a method of promoting adhesion in filled thermoplastic compounds, by incorporating the composition into the filled thermoplastic compounds, (7) a method of treating mineral, organic and metallic surfaces, by applying the composition to a mineral, organic or metallic surface, (8) a method of hydrophobicizing surfaces, by applying the composition to a surface, and (9) a method of surface modifying pulverulent substances, by applying the composition to the surface of a pulverulent substance.

A more complete appreciation of the invention and many of the attendant advantages thereof will be readily obtained as the same becomes better understood by reference to the following detailed description.

DETAILED DESCRIPTION OF THE INVENTION

Resultant mixtures of the invention comprising catenate and cyclic siloxane oligomers are normally homogeneous, clear, colorless to pale yellow liquids of low viscosity which are stable on storage and preferably have a flash point>100° C.

By means of the procedure described above it is possible advantageously to produce siloxane oligomers of the invention possessing, preferably, a statistical distribution of [—Si(R)(R)O—] units of different functionality.

It is also advantageous that the boiling point of the mixtures of the invention comprising catenate and cyclic siloxane oligomers is generally at a temperature >200° C.

The present invention therefore provides a mixture of catenate and cyclic siloxane oligomers of the formulae I and II:

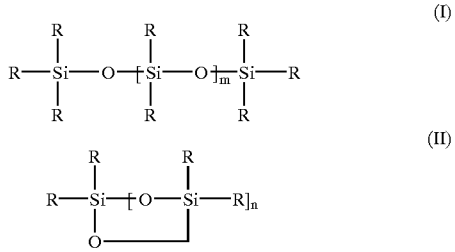

where the substituents R consist of
(i) aminopropyl-functional groups of the formula —$(CH_2)_3$—$NH_2$ or —$(CH_2)_3$—NHR' or —$(CH_2)_3$—NH$(CH_2)_2$—$NH_2$ or —$(CH_2)_3$—NH$(CH_2)_2$—NH$(CH_2)_2$—$NH_2$, in which R' is a linear, branched or cyclic alkyl group of 1 to 18 carbon atoms or an aryl group of 6 to 12 carbon atoms, and (ii) methoxy, ethoxy, 2-methoxyethoxy and/or propoxy groups, and (iii) if desired, alkyl, alkenyl, isoalkyl or cycloalkyl groups of 1 to 18 carbon atoms and/or aryl groups of 6 to 12 carbon atoms, and where not more than one aminopropyl-functional group is attached to one silicon atom and the degree of oligomerization of compounds of the formula I is within the range 2<m<30 and that of compounds of the formula II is 3≦n≦30 and the quotient of the molar proportion of Si/alkoxy group is ≧0.5.

Thus, each R is independently selected from the group consisting of —$(CH_2)_3$—$NH_2$, —$(CH_2)_3$—NHR', —$(CH_2)_3$—NH$(CH_2)_2$—$NH_2$, —$(CH_2)_3$—NH$(CH_2)_2$—NH$(CH_2)_2$—$NH_2$, methoxy, ethoxy 2-methoxyethoxy, propoxy, alkyl, alkenyl, isoalkyl and cycloalkyl groups having 1 to 18 carbon atoms, and aryl groups having 6 to 12 carbon atoms, with at least one R is an aminopropyl-functional group selected from the group consisting of —$(CH_2)_3$—$NH_2$, —$(CH_2)_3$—NHR', —$(CH_2)_3$—NH$(CH_2)_2$—$NH_2$, and —$(CH_2)_3$—NH$(CH_2)_2$—NH$(CH_2)_2$—$NH_2$ groups, and with at least one R is selected from the group consisting of methoxy, ethoxy, 2-methoxyethoxy, and propoxy groups.

Mixtures of the invention comprising catenate and cyclic siloxane oligomers preferably have an alkoxy group content of more than 0.1% by weight and less than 50% by weight, in particular less than 30% by weight, with particular preference from 5 to 25% by weight, based on the weight of the siloxane oligomers present. These weight % ranges include all specific values and subranges therebetween, such as 0.2, 0.5, 1, 2, 8, 10, 15 and 20% by weight.

In a mixture according to the invention, preferably, the substituents R consist of (i) aminopropyl, aminoethylaminopropyl, aminoethylaminoethylaminopropyl, methylaminopropyl, n-butylaminopropyl, cyclohexylaminopropyl and/or phenylaminopropyl groups and (ii) methoxy, ethoxy, 2-methoxyethoxy and/or -propoxy groups, and (iii) optionally, methyl, vinyl, ethyl, propyl, isobutyl, octyl, hexadecyl or phenyl groups.

As examples, preferred systems of catenate and cyclic siloxane oligomers include the following: 3-aminopropyl-/n-propyl-/alkoxy-siloxanes; N-aminoethyl-3-aminopropyl-/n-propyl-/alkoxy-siloxanes; N-butyl-amino-propyl-/methyl-/alkoxy-siloxanes, where the alkoxy groups are preferably methoxy or ethoxy groups although it is also possible for ethoxy and methoxy groups to be present alongside one another.

The present invention also provides a process for preparing a novel mixture of catenate and cyclic siloxane oligomers by controlled hydrolysis using at least one aminopropyl-functional trialkoxysilane or an aminopropyl-functional methyldialkoxysilane as component A and, if desired, at least one alkyl-, alkenyl-, isoalkyl- or cycloalkyl-trialkoxysilane of 1 to 18 carbon atoms and/or phenyltrialkoxysilane and/or alkyl-, alkenyl-, isoalkyl or cycloalkyl-methyldialkoxysilane of 1 to 18 carbon atoms and/or phenylmethyldialkoxysilane as component B and, if desired, a tetraalkoxysilane as component C, subjecting the components A and—if used—B and C in succession or in a mixture to controlled hydrolysis and condensation using from 0.6 to 1.2 mol of water per mole of Si and from 0.1 to 5 times the amount by weight of methanol and/or ethanol, based on the alkoxysilanes employed, at a temperature from 10 to 95° C. and subsequently removing the alcohol employed, and that liberated during the reaction, from the product mixture by distillation under atmospheric pressure or reduced pressure and at a liquid-phase temperature of up to 120° C.

For the preparation of novel mixtures it is possible to start—for example but not exclusively—from the following compounds, or from mixtures of these compounds:

For Component A
3-aminopropyltrialkoxysilanes, N-aminoethyl-3-aminopropyltrialkoxy silanes, N-aminoethyl-N-aminoethyl-3-aminopropyltrialkoxysilanes, N-methylaminopropyl-trialkoxysilanes, N-n-butylaminopropyltrialkoxysilanes, N-cyclohexylaminopropyltrialkoxysilanes, N-phenyl-aminopropyltrialkoxysilanes, 3-aminopropyl-methyldialkoxysilanes, N-aminoethyl-3-aminopropyl-methyldialkoxysilanes, N-aminoethyl-N-aminoethyl-3-aminopropyl-methyldialkoxysilanes, N-methyl-aminopropyl-methyldialkoxysilanes, N-n-butyl-aminopropylmethyldialkoxysilanes, N-cyclohexyl-aminopropylmethyldialkoxysilanes, N-phenyl-aminopropyl-methyldialkoxysilanes.

For component B
methyltrialkoxysilanes, ethyltrialkoxysilanes, n-propyltrialkoxysilanes, isobutyltrialkoxysilanes, n-octyltrialkoxysilanes, isobutyltrialkoxysilanes, n-octyltrialkoxysilanes, isooctyltrialkoxysilanes, hexadecyltrialkoxysilanes, phenyltrialkoxysilanes, vinyl-trialkoxysilanes.

For component C
tetraalkoxysilanes, where abovementioned alkoxy groups are preferably methoxy and ethoxy.

In general, the process of the invention may be performed as follows:

Component A, component B if desired and component C if desired are generally introduced as initial charge into the reaction vessel. A solvent or diluent, such as methanol or ethanol, may be added to the alkoxysilane mixture. It is suitable in addition to add the calculated amount of water for the reaction appropriately with thorough mixing with, for example, stirring. Before or after the addition of water the reaction mixture can be heated and following the reaction the resultant product mixture can be worked up by distillation in the manner described. The distillative workup of the product mixture is preferably conducted under atmospheric pressure and/or reduced pressure at a temperature in the range from 50 to 120° C.

In the process of the invention, components A, B and C are employed preferably in a molar ratio A:B:C of from 1:0:0 to 1:10:0, preferably from 1:0:0 to 1:4:0, or from 1:0:0 to 1:0:10, preferably from 1:0:0 to 1:0:4, or from 1:0:0 to 1:10:10, preferably from 1:0:0 to 1:4:4.

In the process of the invention it is also preferred to employ alkoxysilanes having methoxy or ethoxy groups in accordance with the alcohol that is used as solvent or diluent. The solvent or diluent used is also suitably methanol, ethanol or a mixture of methanol and ethanol. However, other alcohols or alcohol mixtures can also be used.

In the process of the invention the hydrolysis and condensation of the alkoxysilanes employed are conducted preferably under atmospheric pressure at a temperature from 10 to 95° C., with particular preference at from 60 to 80° C. The reaction is normally conducted under atmospheric pressure, although it may also be conducted under reduced pressure or under superatmospheric pressure. It is appropriate to allow the reaction mixture to react for from 2 to 8 hours before beginning the distillation workup of the product mixture.

Following distillative workup, the product of the invention contains preferably less than 5% by weight of the components A, B and C and, in particular, less than 1% by weight of free alcohols.

Novel mixtures of catenate and cyclic siloxane oligomers may be used in the ways set out as described below, which, however, represent only nonlimiting examples.

The present invention therefore provides for the use of a novel mixture of catenate and cyclic siloxane oligomers as a composition for surface modification of pulverulent substances, for silanization of finely divided inorganic fillers and pigments, and also for treating mineral, organic and metallic surfaces, such as concrete, aluminum, steel and plastics (including PVC and PMMA to name but a few), for example. For instance, a novel mixture of catenate and cyclic siloxane oligomers can also be employed advantageously for the hydrophobicization of surfaces. In these applications, and those described below, an amount of the composition effective to accomplish the desired effect is applied.

The present invention additionally provides for the use of a novel mixture of catenate and cyclic siloxane oligomers as adhesion promoters in filled thermoplastic compounds, examples being HFFR (halogen free flame retardants) compounds, in order to provide improved mechanical strength and improved electrical insulation properties.

The present invention provides, moreover, for the use of a novel mixture of catenate and cyclic siloxane oligomers as adhesion promoters in adhesives and sealants in order to provide improved service properties, especially controlled curing behavior, improved mechanical strength and improved moisture resistance.

The invention also provides for the use of a novel mixture of catenate and cyclic siloxane oligomers for modification and crosslinking of organic resins, as binders in coatings and inks having improved service properties. and for coating glass fibers, for improved adhesion of these glass fibers in plastics reinforced with them and for providing improved mechanical strength.

Particularly advantageous properties of the siloxane oligomer mixtures of the invention relative to monomeric aminofunctional silanes employed as standard are the heightened boiling point, the increased flash point, the reduced vapor pressure, the reduced amount of hydrolysis alcohol liberated in the course of use (VOC) and in particular, the chemical "multifunctionality".

Having generally described this invention, a further understanding can be obtained by reference to certain specific examples which are provided herein for purposes of illustration only and are not intended to be limiting unless otherwise specified.

EXAMPLES

Example 1

A 4 l stirred glass reactor with reduced-pressure, metering and distillation apparatus is charged with 1791 g of 3-aminopropyltrimethoxysilane (AMMO) and 820.5 g of n-propyltrimethoxysilane (PTMO). 216.0 g of water and 300.0 g of methanol are mixed and the mixture is added over the course of 20 minutes via the metering device. The reaction mixture heats up from room temperature to about 70° C. It is subsequently stirred at about 65° C. for 5 hours and then methanol is distilled off under reduced pressure (liquid-phase temperature 50 to 70° C., pressure falling from 400 to 10 hPa) over 2 hours. This gives 1924 g of a colorless and clear liquid having the following characteristics:

| | |
|---|---|
| Free MeOH (by gas chromatography): | 0.3% by weight |
| Silicon: | 20.8% by weight |

-continued

| | |
|---|---|
| Nitrogen: | 6.9% by weight |
| Viscosity: | 35 mPa s (DIN 53 015) |
| Flash point: | 115° C. (DIN 51 755) |
| Density: | 1.103 g/ml (DIN 51 757) |
| Average molar mass (gel permeation chromatography): | 1000 g/mol |

Example 2

A 2 l stirred glass reactor with reduced-pressure, metering and distillation apparatus is charged with 246 g of n-propyltrimethoxysilane (PTMO) and this initial charge is heated to 80° C. 21.6 g of water and 144.2 g of methanol are mixed and added via the metering device over the course of 30 minutes. During this addition there is no change in the temperature of the reaction mixture. After the end of addition of the water/methanol mixture, the reaction mixture is stirred at 80° C. for 2 hours. Then, at 80° C., 667 g of ethylenediaminopropyl-trimethoxysilane (DAMO) are added and the mixture is stirred for 30 minutes. Then a mixture of 43.2 g of water and 288.4 g of methanol is added over 30 minutes and the reaction mixture is stirred at 80° C. for 1 hour.

The methanol in the reaction mixture is removed by distillation, first at atmospheric pressure (about 300 g over 3 hours) and then the remainder under reduced pressure (liquid-phase temperature 70 to 90° C., pressure falling from 450 to 1 hPa) over 3 hours. This is followed by a reduced-pressure aftertreatment for 1 hour at 1 hPa and a liquid-phase temperature of about 110° C. This gives 690 g of a clear yellow liquid having the following characteristics:

| | |
|---|---|
| Free MeOH (by gas chromatography): | <0.1% by weight |
| Silicon: | 17.3% by weight |
| Nitrogen: | 10.8% by weight |
| Viscosity: | 208 mPa s (DIN 53 015) |
| Boiling point: | 267° C. (ASTM D-1120) |
| Flash point: | 136° C. (DIN 51 755) |
| Density: | 1.096 g/ml (DIN 51 757) |
| Total chloride content: | 88 mg/kg |
| Average molar mass (gel permeation chromatography): | about 1000 g/mol |

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 19849308.8, filed on Oct. 27, 1998, and incorporated herein by reference.

What is claimed is:

1. A process for preparing a mixture of at least one catenate siloxane oligomer represented by formula (I) and at least one cyclic siloxane oligomer represented by formula (II):

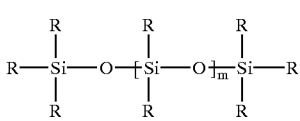

(I)

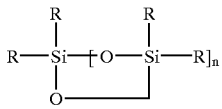

(II)

wherein each R is independently selected from the group consisting of —(CH$_2$)$_3$—NH$_2$, —(CH$_2$)$_3$—NHR',—(CH$_2$)$_3$—NH(CH$_2$)$_2$—NH$_2$,—(CH$_2$)$_3$—NH(CH$_2$)$_2$—NH(CH$_2$)$_2$—NH$_2$, methoxy, ethoxy, 2-methoxyethoxy, propoxy, alkyl, alkenyl, isoalkyl and cycloalkyl groups having 1 to 18 carbon atoms, and aryl groups having 6 to 12 carbon atoms, and wherein R' is a linear, branched or cyclic alkyl group having 1 to 18 carbon atoms or an aryl group having 6 to 12 carbon atoms; the degree of oligomerization of compounds represented by formula (I), m, is within the range 2<m<30, and the degree of oligomerization of compounds represented by formula (II), n, is within the range 3<n<30, wherein at least one R is an aminopropyl-functional group selected from the group consisting of —(CH$_2$)$_3$—NH$_2$, —(CH$_2$)$_3$—NHR', —(CH$_2$)$_3$—NH(CH$_2$)$_2$—NH$_2$, and —(CH$_2$)$_3$—NH(CH$_2$)$_2$—NH(CH$_2$)$_2$—NH$_2$ and at least one R is selected from the group consisting of methoxy, ethoxy, 2-methoxyethoxy, propoxy, and not more than one aminopropyl-functional group is attached to one silicon atom, prepared by:

reacting (A) at least one aminopropyl-functional trialkoxysilane or an aminopropyl-functional methyldialkoxysilane, wherein said aminopropyl-functional group is selected from the group consisting of —(CH$_2$)$_3$—NH$_2$, —(CH$_2$)$_3$—NHR', —(CH$_2$)$_3$—NH(CH$_2$)$_2$—NH$_2$, and —(CH$_2$)$_3$—NH(CH$_2$)$_2$—NH(CH$_2$)$_2$—NH$_2$, and said alkoxy groups are selected from the group consisting of methoxy, ethoxy, 2-methoxyethoxy, and propoxy, (B) at least one alkyl-, alkenyl-, isoalkyl- or cycloalkyl-trialkoxysilane having 1 to 18 carbon atoms and/or phenyltrialkoxysilane and/or alkyl-, alkenyl-, isoalkyl- or cycloalkyl-methyldialkoxysilane having 1 to 18 carbon atoms and/or phenylmethyldialkoxysilane, and (C) at least one tetraalkoxysilane in a molar ratio of A:B:C of 1:0:0 to 1:10:0 or 1:0:0 to 1:0:10 or 1:0:0 to :1:10:10 with from 0.6 to 1.2 mol. of water per mol. of Si and from 0.1 to 5 times the amount by weight of methanol and/or ethanol, based on the alkoxysilanes employed, at a temperature from 10 to 95° C., and subsequently removing alcohol from the product mixture by distillation under atmospheric pressure or reduced pressure and at a liquid-phase temperature of up to 120° C.

2. The process of claim 1, wherein (B) at least one alkyl-, alkenyl-, isoalkyl- or cycloalkyl-trialkoxysilane having 1 to 18 carbon atoms and/or phenyltrialkoxysilane and/or alkyl-, alkenyl-, isoalkyl- or cycloalkyl-methyldialkoxysilane having 1 to 18 carbon atoms and/or phenylmethyldialkoxysilane is also coreacted with (A) in said reacting.

3. The process of claim 1, wherein (C) at least one tetraalkoxysilane is also coreacted with (A) in said reacting.

4. The process of claim 1, wherein (B) at least one alkyl-, alkenyl-, isoalkyl- or cycloalkyl-trialkoxysilane having 1 to 18 carbon atoms and/or phenyltrialkoxysilane and/or alkyl-, alkenyl-, isoalkyl- or cycloalkyl-methyldialkoxysilane having 1 to 18 carbon atoms and/or phenylmethyldialkoxysilane and (C) at least one tetraalkoxysilane are also coreacted with (A) in said reacting.

5. The process of claim 1, wherein alkoxysilanes having methoxy or ethoxy groups in accordance with the alcohol that is used as solvent or diluent are employed.

6. The process of claim 1, wherein the reacting is conducted under atmospheric pressure at a temperature from 10 to 95° C.

7. The process of claim 1, wherein the distillative workup of the product mixture is conducted under atmospheric pressure and/or reduced pressure at a temperature in the range from 50 to 120° C.

8. The process of claim 1, wherein the product obtained following distillation workup contains less than 5% by weight of the components A, B and C employed and less than 1% by weight of free alcohols.

9. The process of claim 1, wherein (A) is selected from the group consisting of 3-aminopropyltrialkoxysilanes, N-aminoethyl-3-aminopropyltrialkoxy silanes, N-aminoethyl-N-aminoethyl-3-aminopropyltrialkoxysilanes, N-methylaminopropyltrialkoxysilanes, N-n-butylaminopropyltrialkoxysilanes, N-cyclohexylamino-propyltrialkoxysilanes, N-phenylaminopropyltrialkoxysilanes, 3-aminopropylmethyldialkoxysilanes, N-aminoethyl-3-aminopropylmethyldialkoxysilanes, N-aminoethyl-N-aminoethyl-3-aminopropylmethyldialkoxysilanes, N-methyl-aminopropyl-methyldialkoxysilanes, N-n-butyl-aminopropylmethyldialkoxysilanes, N-cyclohexyl-aminopropylmethyldialkoxysilanes, and N-phenyl-aminopropyl-methyldialkoxysilanes.

10. The process of claim 2, wherein (B) is selected from the group consisting of methyltrialkoxysilanes, ethyltrialkoxysilanes, n-propyltrialkoxysilanes, isobutyltrialkoxysilanes, n-octyltrialkoxysilanes, isobutyltrialkoxysilanes, n-octyltrialkoxysilanes, isooctyltrialkoxysilanes, hexadecyltrialkoxysilanes, phenyltrialkoxysilanes, and vinyltrialkoxysilanes.

11. The process of claim 1, wherein the alkoxy moieties of (A) are, independently, methoxy or ethoxy.

12. The process of claim 2, wherein the alkoxy moieties of (B) are, independently, methoxy or ethoxy.

13. The process of claim 4, wherein the alkoxy moieties of (C) are, independently, methoxy or ethoxy.

14. A mixture of at least one catenate siloxane oligomer represented by formula (I) and at least one cyclic siloxane oligomer represented by formula (II):

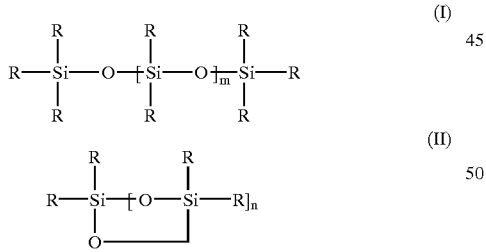

wherein each R is independently selected from the group consisting of —(CH$_2$)$_3$—NH$_2$, —(CH$_2$)$_3$—NHR',—(CH$_2$)—NH(CH$_2$)$_2$—NH$_2$—(CH$_2$)$_3$—NH(CH$_2$)$_2$—NH(CH$_2$)$_2$—NH$_2$, methoxy, ethoxy, 2-methoxyethoxy, propoxy, alkyl, alkenyl, isoalkyl and cycloalkyl groups having 1 to 18 carbon atoms, and aryl groups having 6 to 12 carbon atoms, and wherein R' is a linear, branched or cyclic alkyl group having 1 to 18 carbon atoms or an aryl group having 6 to 12 carbon atoms; the degree of oligomerization of compounds represented by formula (I), m, is within the range 2<m<30, and the degree of oligomerization of compounds represented by formula (II), n, is within the range 3≦n≦30, wherein at least one R is an aminopropyl-functional group selected from the group consisting of —(CH$_2$)$_3$—NH$_2$, —(CH$_2$)$_3$—NHR', —(CH$_2$)$_3$—NH(CH$_2$)$_2$—NH$_2$, and —(CH$_2$)$_3$—NH(CH$_2$)$_2$—NH(CH$_2$)$_2$—NH$_2$ and at least one R is selected from the group consisting of methoxy, ethoxy, 2-methoxyethoxy, propoxy, and not more than one aminopropyl-functional group is attached to one silicon atom, prepared by:

reacting (A) at least one aminopropyl-functional trialkoxysilane or an aminopropyl-functional methyldialkoxysilane, wherein said aminopropyl-functional group is selected from the group consisting of —(CH$_2$)$_3$—NH$_2$, —(CH$_2$)$_3$—NHR', —(CH$_2$)$_3$—NH(CH$_2$)$_2$—NH$_2$, and —(CH$_2$)$_3$—NH(CH$_2$)$_2$—NH(CH$_2$)$_2$—NH$_2$, and said alkoxy groups are selected from the group consisting of methoxy, ethoxy, 2-methoxyethoxy, and propoxy, (B) at least one alkyl-, alkenyl-, isoalkyl- or cycloalkyl-trialkoxysilane having 1 to 18 carbon atoms and/or phenyltrialkoxysilane and/or alkyl-, alkenyl-, isoalkyl- or cycloalkyl-methyldialkoxysilane having 1 to 18 carbon atoms and/or phenylmethyldialkoxysilane, and (C) at least one tetraalkoxysilane in a molar ratio of A:B:C of 1:0:0 to 1:10:0 or 1:0:0 to 1:0:10 or 1:0:0 to 1:10:10 with from 0.6 to 1.2 mol. of water per mol. of Si and from 0.1 to 5 times the amount by weight of methanol and/or ethanol, based on the alkoxysilanes employed, and subsequently removing alcohol from the product mixture.

15. The composition of claim 14, which has an alkoxy group content of more than 0.1% by weight and less than 50% by weight, based on the weight of the siloxane oligomer mixture present.

16. The composition of claim 14, wherein each R is independently selected from the group consisting of aminopropyl, aminoethylaminopropyl, aminoethylaminoethylaminopropyl, methylaminopropyl, n-butylaminopropyl, cyclohexylaminopropyl, phenylaminopropyl, methoxy, ethoxy, 2-methoxyethoxy, propoxy, methyl, ethyl, vinyl, propyl, isobutyl, octyl, hexadecyl, and phenyl groups, at least one R is selected from the group consisting of aminopropyl, aminoethylaminopropyl, aminoethylaminoethylaminopropyl, methylaminopropyl, n-butylaminopropyl, cyclohexylaminopropyl, and phenylaminopropyl groups, and at least one R is selected from the group consisting of methoxy, ethoxy, 2-methoxyethoxy, and propoxy groups.

17. The composition of claim 14, which has a boiling point >200° C.

18. The composition of claim 14, which has a flash point >100° C.

19. The composition of claim 14, wherein each R is independently selected from the group consisting of —(CH$_2$)$_3$—NH$_2$, —(CH$_2$)$_3$—NHR', —(CH$_2$)$_3$—NH(CH$_2$)$_2$—NH$_2$, (CH$_2$)$_3$—NH(CH$_2$)$_2$—NH(CH$_2$)$_2$—NH$_2$, methoxy, ethoxy, 2-methoxyethoxy, and propoxy groups.

20. The composition of claim 14, wherein each R is independently selected from the group consisting of —(CH$_2$)$_3$—NH$_2$, —(CH$_2$)$_3$—NHR', —(CH$_2$)$_3$—NH(CH$_2$)$_2$—NH$_2$, —(CH$_2$)$_3$—NH(CH$_2$)$_2$—NH(CH$_2$)$_2$—NH$_2$, methoxy, ethoxy, and propoxy groups.

21. A method of improving the adhesion properties of adhesives and sealants, comprising incorporating the mixture of claim 14, into an adhesive or a sealant.

22. A method of modifying organic resins, comprising contacting an organic resin with the mixture of claim 14.

23. A method of crosslinking organic resins, comprising contacting the organic resins with the mixture of claim 14.

24. A method of providing binders in inks and coatings, comprising incorporating the mixture of claim 14 into an ink or a coating.

25. A method of coating glass fibers, comprising applying the mixture of claim 14 to glass fiber.

26. A method of promoting adhesion in filled thermoplastic compounds, comprising incorporating the mixture of claim 14 into the filled thermoplastic compounds.

27. A method of treating mineral, organic and metallic surfaces, comprising applying the mixture of claim 14 to a mineral, organic or metallic surface.

28. A method of hydrophobicizing surfaces, comprising applying the mixture of claim 14 to a surface.

29. A method of surface modifying pulverulent substances, comprising applying the mixture of claim 14 to the surface of a pulverulent substance.

* * * * *